US009492640B2

United States Patent
Rosenhan

(10) Patent No.: US 9,492,640 B2
(45) Date of Patent: Nov. 15, 2016

(54) CATHETER SECUREMENT DEVICE AND METHODS

(71) Applicant: SimplicityMD Solutions, LLC, Bountiful, UT (US)

(72) Inventor: Branden D. Rosenhan, Salt Lake City, UT (US)

(73) Assignee: SIMPLICITYMD SOLUTIONS, LLC, Salt Lake City, UT (US)

( * ) Notice: Subject to any disclaimer, the term of this patent is extended or adjusted under 35 U.S.C. 154(b) by 0 days.

(21) Appl. No.: 14/537,902

(22) Filed: Nov. 10, 2014

(65) Prior Publication Data

US 2015/0133891 A1    May 14, 2015

Related U.S. Application Data

(60) Provisional application No. 61/902,224, filed on Nov. 9, 2013, provisional application No. 62/001,629, filed on May 21, 2014.

(51) Int. Cl.
*A61M 25/02* (2006.01)

(52) U.S. Cl.
CPC ........ *A61M 25/02* (2013.01); *A61M 2025/024* (2013.01); *A61M 2025/0246* (2013.01); *A61M 2025/0266* (2013.01); *A61M 2025/0286* (2013.01)

(58) Field of Classification Search
CPC ............... A61M 2025/024; A61M 2025/0246; A61M 2025/0266; A61M 2025/0286; A61M 25/02
See application file for complete search history.

(56) References Cited

U.S. PATENT DOCUMENTS

| | | | |
|---|---|---|---|
| 5,026,352 A | 6/1991 | Anderson | |
| 5,690,616 A | 11/1997 | Mogg | |
| 5,713,869 A | 2/1998 | Morejon | |
| 6,001,081 A | 12/1999 | Collen | |
| 7,709,694 B2 | 5/2010 | Batich et al. | |
| 8,269,058 B2 | 9/2012 | McCarthy et al. | |
| 8,277,417 B2 * | 10/2012 | Fedinec | A61B 8/0841 600/585 |
| 8,640,738 B2 * | 2/2014 | Zia | A61M 5/1418 138/103 |
| 8,834,426 B2 * | 9/2014 | Shipman | A61L 29/06 604/180 |

(Continued)

FOREIGN PATENT DOCUMENTS

| WO | WO/02/061318 | 8/2002 |
|---|---|---|
| WO | WO/03/035160 | 5/2003 |

OTHER PUBLICATIONS

International Search Report of PCT/US2012/036963, mailed Aug. 17, 2012.

(Continued)

*Primary Examiner* — Aarti B Berdichevsky
(74) *Attorney, Agent, or Firm* — Workman Nydegger

(57) ABSTRACT

A catheter securement device includes a body having a generally curved channel configured to receive a central venous catheter and reposition it in a different direction than the direction of the catheter as it exits the skin of the patient. The securement device includes a cover that slidably connects to the securement device body to prevent the catheter from being pulled out of the curved channel.

20 Claims, 3 Drawing Sheets

(56) References Cited

U.S. PATENT DOCUMENTS

2006/0047268 A1 3/2006 Stephens
2010/0174240 A1 7/2010 Wells et al.
2014/0128813 A1* 5/2014 Rosenhan ............. A61M 25/02
                                                                          604/174

OTHER PUBLICATIONS

Extended European Search Report of EP 2707065, mailed Sep. 19, 2014.

* cited by examiner

CATHETER SECUREMENT DEVICE AND METHODS

CROSS-REFERENCE TO RELATED APPLICATIONS

This Application claims the benefit of U.S. provisional patent Application No. 61/902,224, filed Nov. 9, 2013 and 62/001,629 filed May 21, 2014, both titled Catheter Securement Device and Related Methods," and both of which are hereby incorporated herein by reference in their entirety.

BACKGROUND

A central line catheter ("central venous catheter", "CVC", "central venous line" or "central venous access catheter") or midline catheter (a venous catheter placed in similar locations but not terminating in a central vein) are catheters placed into a large vein in the neck (internal jugular vein or external jugular vein), chest (subclavian vein) or groin (femoral vein). Central and midline venous catheters are typically used to administer medication or fluids, obtain blood tests (specifically the "mixed venous oxygen saturation"), and directly obtain cardiovascular measurements such as the central venous pressure. As used herein the term "catheter" may also refer to a tube designed to drain fluid or material within the abdomen, pelvis, chest or other body cavities, such as are use in pulmonology, critical care, general surgery, orthopedic surgery, interventional radiology and other such specialties where catheters are placed with the primary intent to drain material and not infuse material.

In cases of long term infusion or the long term placement of testing equipment, it is typically necessary for the catheter to remain in place for many days. In order to secure such a central line catheter in position at the injection site, the IV tubing is commonly mounted on a thin flexible pad or seat that is sutured to the patient's skin. This combination of tubing and pad comprises a connector to which one or more other IV supply lines having compatible connectors can be attached.

An example of such an anchor is shown in FIGS. 1-3 labeled generally 2. The anchor 2 has a tubular body 4 and a pair of opposed wings 6. Body 4 has a central channel 8. Central channel 8 is typically sized to be the same diameter as the outer diameter of a catheter 14 (e.g., a multi-lumen catheter having multiple access ports) that is to be secured by the anchor 2. Body 4 often has a longitudinal slit 10 that extends entirely through body 4 along the entire length of body 4. The longitudinal slit 10 is typically placed in the body 4 to allow the anchor to be slipped over the catheter 14 after the catheter 14 is installed in the patient's body (e.g., in the external jugular vein).

The wings 6 of the anchor 2 each have an eyelet 12. In use, a catheter 14 is placed through slit 10 into channel 8. Because of the tight tolerance in the diameter of central channel 8 and the outer diameter of catheter 14, it is very difficult if not impossible to thread catheter 14 through channel 8. Thereafter, anchor 2 is moved to the desired position. Wings 6 are pinched together toward slit 10. A suture 16 is placed through eyelets 12 and tissue into the patient's tissue (not shown) to secure the catheter 14 and the anchor 2 to the patient's tissue.

When the central line catheter is positioned in the jugular vein using the anchor 2 described above, the internal end of the catheter enters the neck of the patient and the external end exits the neck and extends toward the patient's head. A number of problems, however, have arisen with respect to such placement. For example, the location of the access ports can be uncomfortable for the patient and inconvenient for medical personnel to access. In addition, the access ports can extend into the patient's hair and ear, which is a potential route for contamination or infection of the central line. If the patient is of shorter stature, more of the catheter will protrude out of the body and securing the catheter may require suturing or stapling at an inconvenient site very near to or directly under the patient's upper neck, jaw, or ear. Additionally, this current method does little to address the potential for infection at the site where the catheter is inserted under the skin.

BRIEF DESCRIPTION OF THE DRAWINGS

To further clarify the above and other advantages and features of the present disclosure, a more particular description of the embodiments of the invention will be rendered by reference to specific embodiments thereof which are illustrated in the appended drawings. It is appreciated that these drawings depict only illustrated embodiments of the invention and are therefore not to be considered limiting of its scope. The embodiments of the invention will be described and explained with additional specificity and detail through the use of the accompanying drawings in which.

DESCRIPTION

The present disclosure relates to catheter securement devices that have a channel for creating a curve (i.e., bend) in a catheter without causing kinking. For example, the securement device may have a generally curved channel extends from a first end to a second end and is configured for receiving a portion of a catheter to secure the catheter to a patient's body. The securement device may be used to secure a catheter that has an end inserted into a vessel of a patient's body (e.g., a central line catheter, such as a multi-lumen central line catheter). The catheter body causes the catheter to adopt a bent profile that redirects the free end of the catheter away from the direction of catheter exiting the skin, which, for example, reduces the likelihood that the catheter will be accidentally pulled out or dislodged if the free end of the catheter is pulled on. Likewise, the curved channel of the catheter securement device supports the bent profile to greatly reduce risk of kinking the catheter.

The devices of the invention can be used with central line catheters. Central line catheter is installed at an interior jugular location, the catheter securement device allows the free end of the catheter to safely hang down away from the patient's hair and ear for greater patient comfort, ease of access by medical personnel, and reduced danger of infection. Such positioning will also be advantageous to patients, allowing them to freely move without discomfort or limitation. Likewise, when laying in a hospital bed the likelihood of patients rolling over onto the catheter ports when turning will be greatly reduced.

In another embodiment, the present invention relates to a method for securing a central line catheter to a patient's skin. The method includes (1) positioning a catheter in a body lumen or a body cavity of a patient, (2) positioning a free end of the catheter in a catheter securement device as described herein, and (3) securing the catheter securement device to the patient's skin.

In yet another embodiment, a kit is described. The kit may include but is not limited to, a catheter, apparatus for inserting the catheter into a body lumen or a body cavity of a patient, and a catheter securement device as described herein.

Figure 1:
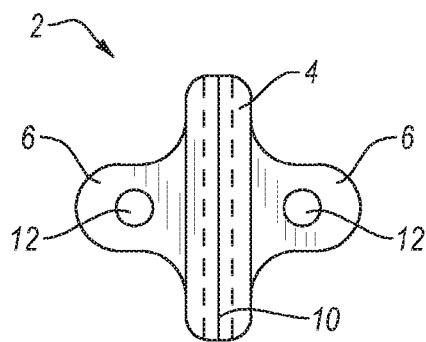
FIG. 1 illustrates a top view of a prior art catheter securement device.
Figure 2:
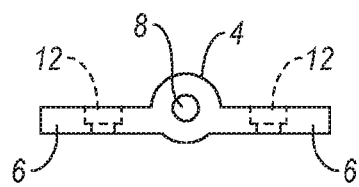
FIG. 2 illustrates an end on view of the catheter securement device of FIG. 1.
Figure 3:
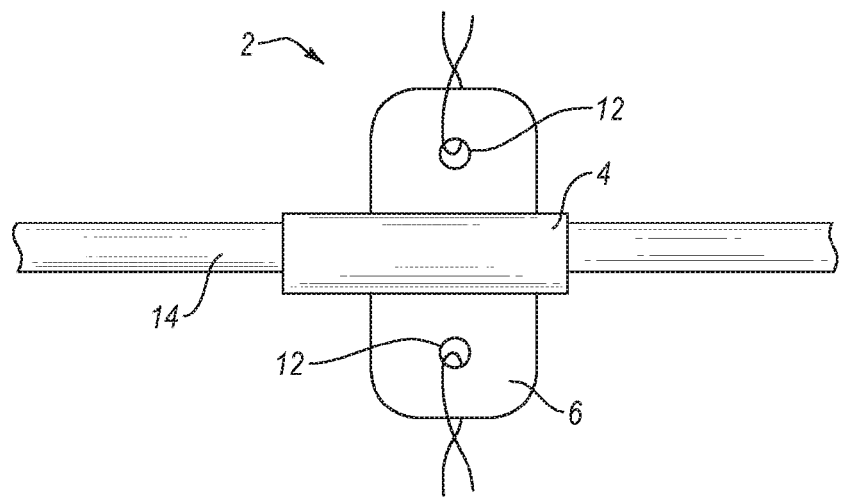
FIG. 3 illustrates the catheter securement device of FIG. 1 in use with a catheter.
Figure 4:
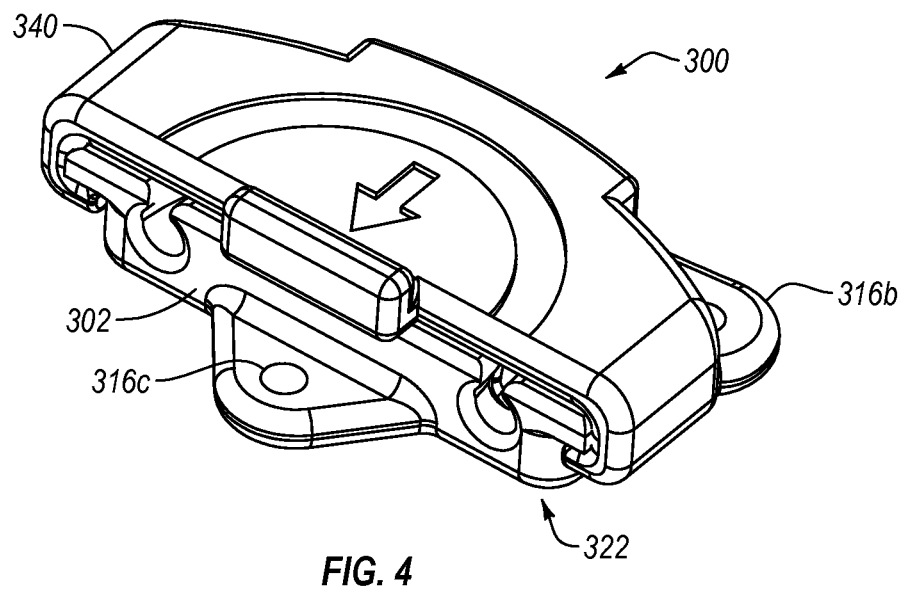
FIG. 4 is a perspective view of a catheter securement device according to one embodiment.
Figure 5:
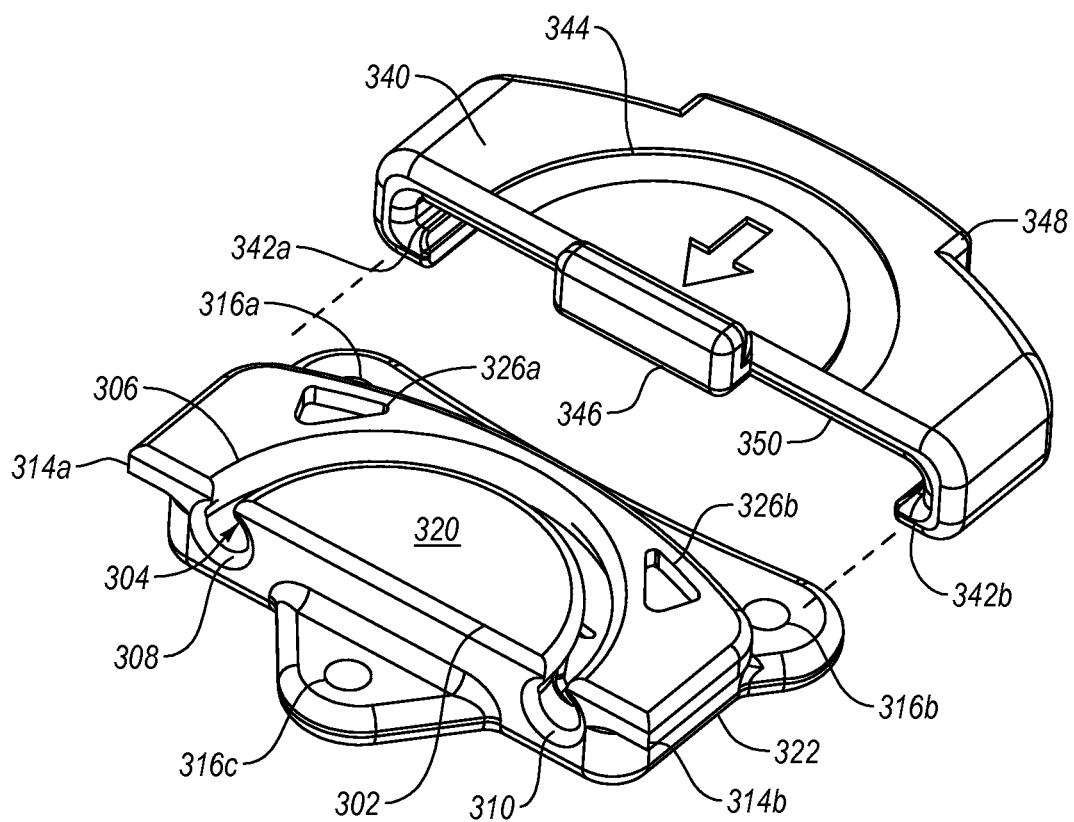
FIG. 5 is an exploded view of the catheter securement device of FIG. 4.
Figure 6:
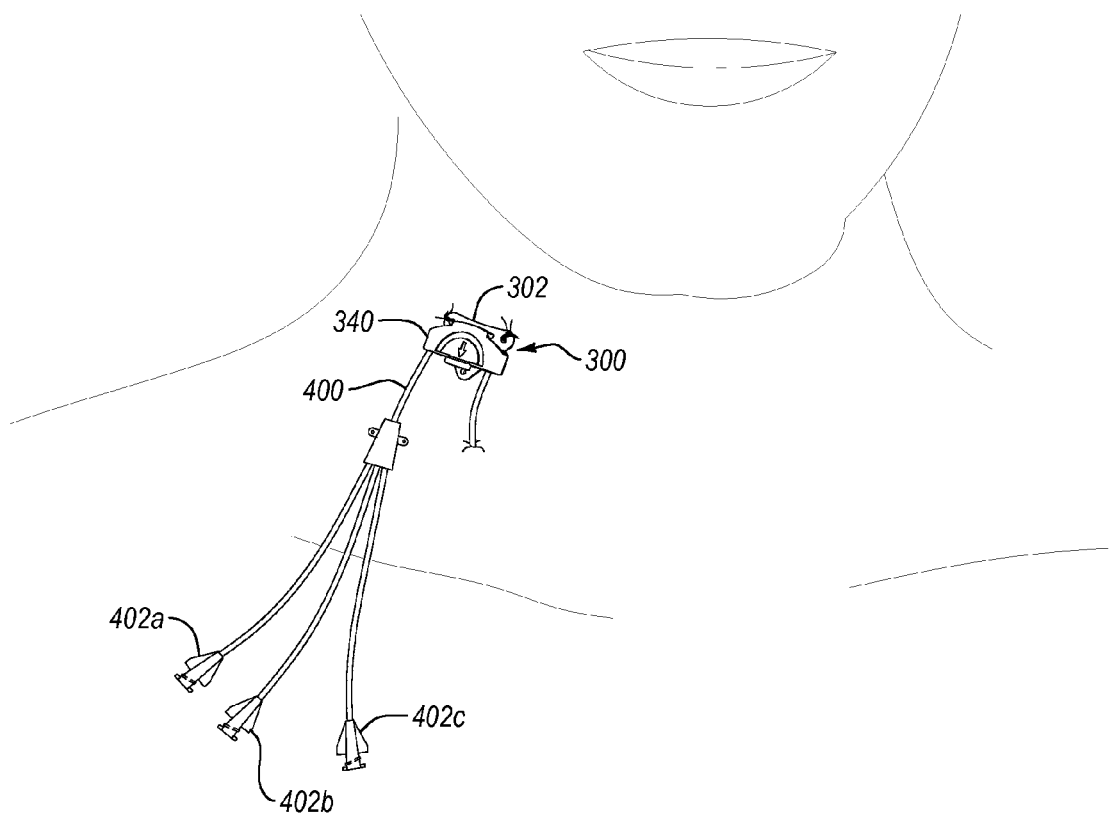
FIG. 6 illustrates the use of the catheter securement device of FIG. 4 on a patient with a central venous catheter placed in the internal jugular vein.

FIGS. 4-6 illustrate an embodiment of a catheter securement device 300 that has a body 302 that releasably couples with a cover 340. Body 302 has a top surface 320 that is opposite a bottom surface 322 that faces the surface of a patient during use (i.e., the skin surface). Body 302 defines a channel 304 having an opening 306 (e.g., a top opening that is parallel to the surface of the patient of a skin when the device is affixed to the skin). Channel 304 and its opening 306 extend from first end 308 to second end 310 and are sized and configured to receive a portion of the tubing of a catheter. Eyelets 318a, 318b, and 318c provide an attachment site for sutures to be looped through the securement device and into a person's skin for attaching the device to the skin.

Cover 340 and body 302 are configured to slidably engage one another. Cover 340 when engaged with body 302 prevents a catheter from exiting channel 304 when the free end of the catheter is pulled. In one embodiment, cover 340 slidably engages body 302 transverse to opening 306. By engaging in the transverse direction, a force in the parallel direction does not cause the cover to disengage. As shown in FIG. 5, body 302 may include extensions 314a and 314b extend laterally on body 302 to form undercuts. Extensions 314 are configured to slidably engage flanges 342a and 342b of cover 340. Cover 340 slides onto body 340 from the side opposite the side where the catheter exits such that the loose ends of the catheter do not interfere with placement of the cover. Cover 340 can include a translucent or transparent portion that allows the catheter to be viewed when cover 340 is in place. For example, cover 340 includes a translucent arc 344. Cover 340 can also include protrusions 346 and 348 that provide a surface for engaging cover 340 to apply and/or remove cover 340 from body 302. In one embodiment, protrusion 346 may extend upward, but flush with edge 350 to avoid interfering with eyelet 316c.

Base 302 may include indentions 326a and 326b that form a bump lock with cover 340. Cover 340 may have protrusions on its underside to engage the indentations. When cover 340 is coupled with body 302 as shown in FIG. 4, indentions 326a and 326b engage cover 304 and prevent it from sliding back off without appropriate force by a user.

The following describes general features that can be used in the foregoing and similar catheter securement devices according to various embodiments of the invention.

In one embodiment, the securement device may define a curved channel with a radius of about 1.5 to about 3 cm, but may be as long as 5 cm to accommodate larger catheters. However, it will be understood that the curved channel can be larger or smaller depending on the diameter of the catheter to be affixed to the body. For example, the curved channel and the channel formed therein can be configured to accommodate a catheter having a size greater than 2, 3, 4, 5, or 6 French and/or less than 20, 15, 12, 8, or 6 French, or within a range of any of the foregoing sizes. For example, the channel may accommodate and grip a channel in a range from about 5 French to about 15 French, or about 7 French to about 9 French. In another example, the channel can be sized with an inner radius of curvature sized to accommodate a catheter having a size in a range from about 5 French to about 7 French and an outer radius of curvature sized to accommodate a catheter having a size in a range from about 9 French to about 11 French. In yet another example, the curved channel includes a pliable material in the channel configured to accommodate and retain catheters having sizes ranging from about 5 French to about 15 French.

In one embodiment, the curved channel bends the catheter at an angle in a range between about 90° and about 210°, or any angle therebetween. For example, the curved channel may define an angle of about 90°, 95°, 100°, 105°, 110°, 115°, 120°, 125°, 130°, 135°, 140°, 145°, 150°, 155°, 160°, 165°, 170°, 175°, 180°, 185°, 190°, 195°, 200°, 205°, or 210° of any range of angles between the forgoing angles. Preferably, the curved channel defines an angle of about 135° or 180°.

Examples of catheters that can be used in the present invention include catheters that have a first end, and a second end, where a portion of the catheter at the second end extends under a patient's skin and into a blood vessel. The first end includes a number of ports (e.g., 1, 2, or 3 ports) in fluid communication with separate lumens in the catheter tubing. The ports can include Luer lock hubs or other mechanisms for attaching a syringe or another device for injection or withdrawal of substances through a selected lumen of the catheter. Likewise, one or all of the hubs can be sealed when they are not being used to prevent blood or fluid loss from the patient and/or to prevent infection.

In some embodiments of the invention the hardness of the catheter securement device material may be selected in combination with wall thickness to give the securement device flexibility that provides patient comfort while avoiding kinking of the catheter. The securement device material may have a shore hardness greater than 40 A, 60 A, 80 A, and less than 85 D, 70 D, 50 D or within a range thereof and a wall thickness greater than 10, 25, 40, 60 thousandths, and less than 200, 150, 120, or 100 thousandths of an inch, or within a range thereof. In some embodiments, the body 302 may be softer or more pliable than cover 340. In this embodiment, the body 302 can be flexible to accommodate the catheter and/or the skin of the patient and the cover can provide rigidity. For example, the body 302 may be made from a silicone or urethane and the cover may be made from a more rigid plastic such as ABS or polycarbonate.

In some embodiments, at least a portion of the channel is configured to circumferentially accommodate a particularly sized catheter (i.e., at least a portion of the channel is tube-like). The device may have a channel wall that extends circumferentially around a catheter by at least 160, 170, 180, or preferably at least 181, 185, 190, 200, 205, 210, 220, 240 degrees and/or less than 270, 250, 230, or 210 degrees or within a range thereof (i.e., has an opening that is 360 degrees minus the forgoing values). In some embodiments, at least and/or less than 10%, 30%, 50%, 80%, or 90% of the catheter in the channel is encircled as described herein and/or a range of the foregoing percentages.

In some embodiments opening 306 is less than the diameter of channel 304. The flexibility of the body material may be selected to allow the opening to flex outward to allow the catheter to be inserted. During manufacturing, the flexibility can also facilitate release of the product from a mold (bump mold).

In one embodiment, the channel may be sized to cause better grip. In this embodiment, the curved channel may have a size that is slightly smaller than the catheter. The channel may be at least 5%, 10%, 15%, or 20% smaller than the catheter to be secured and/or less than 30%, 25%, 20%, or 15% or within a range thereof. Preferably, channels that are smaller than the catheter are also made from a flexible material to allow the channel to expand to accommodate the catheter without crushing the catheter, but creating pressure to grip the catheter. Where the securement device is more rigid, the channel may be smaller than the catheter diameter, but closer to the same size as the catheter (e.g., less than 10%, 5%, or 2% smaller).

Channel 304 may also have a surface friction pattern that grips the catheter and/or otherwise reduces pistoning of the catheter within the securement device. The friction pattern may be serrations, bumps, protrusions, scaling (e.g., shark scale pattern) on the surface of the securement device where the catheter is in contact during use (e.g., within the channel). The friction pattern may be molded into the body of the securement device or may be applied to the surface of the securement device material after molding.

In addition to surface features, the length of the channel in contact with the catheter and the extent to which the catheter securement device encircles the catheter may determine in part the difficulty with which the catheter can be moved within the channel (i.e., the tendency for pistoning). In some embodiments, the length of the channel may be greater than or equal to 0.5, 0.75, 1.0, 1.25, 1.5, or 2 inches and/or less than or equal to 3, 2.5, 2, or 1.75 inches or within a range thereof.

The securement device preferably has a low profile. In some embodiments, the height (i.e., standoff from the surface of the skin of a patient) is greater than 0.1, 0.15, 0.2, 0.25, and/or less than 0.8, 0.6, 0.4, or 0.35 inches or within a range thereof.

In some embodiments bottom surface 322 may have an adhesive pad to adhere the securement device to the skin. The adhesive may be used with or without eyelets and/or stitching. In some embodiments body 302 may be rigid and the pad applied to bottom surface 302 may provide sufficient padding to avoid harming the skin of the patient.

Securement device 300 may include an antimicrobial agent coated on a surface thereof or impregnated into the material. For example, the material of channel 304 may include an antimicrobial agent. Alternatively, cover 340 may include an antimicrobial agent. The antimicrobial agent may be applied to the underside such that the antimicrobial agent comes into direct contact with the catheter and/or channel. Placing the antimicrobial agent on the cover 340 can simplify the process for reapplying the antimicrobial agent after the securement device has been applied for a period of time. Instead of replacing the entire device and risking disturbing the catheter, the cover can be replaced to reapply the antimicrobial agent or to allow temporary access to the catheter for cleaning or inspection. Any antimicrobial known in the art can be used, including, but not limited to chlorhexidine.

The securement device can be particularly advantageous when used for placing catheters into the internal jugular vein. Internal jugular catheters are susceptible to infection from ports positioned near the neck and hair. By turning the catheter to face down, the ports lie close to the chest where they are less likely to be tangled and/or contaminated. Figure illustrates a triple lumen central line catheter 400 placed into the skin of patient and inserted into the jugular vein with the tip of the catheter positioned near the heart (e.g., in the superior vena cava). Catheter 400 includes 3 ports 402a, 402b, and 402c. Catheter 400 is secured to the skin of the patent using securement device 300 having a body 302 that is sutured to the patient and a cover 340 that locks the catheter into body 302. In one embodiment, a method includes placing central venous catheter 400 in the internal jugular vein of the patient. The catheter is then placed in a channel of body 302, which redirects the catheter downward. A cap 340 is applied to body 302. Sutures are then placed in body 302 and the skin of the patient to secure device 300 to the skin of the patient.

The present invention includes kits. The kits can include any of the catheter securement devices described herein and a procedure tray, a catheter, and an apparatus for inserting the catheter into a body lumen (e.g., a vein) or a body cavity (e.g., an abdominal cavity) of a patient.

The kit may also include one or more of an anesthetic, a sterilizer for the patient's skin, a needle and suture or staples, a guide wire, a hollow or 'cook' needle for central venous puncture, a dilator, and a scalpel. Apparatus for inserting the catheter may further include a suture needle and a length of suture, a surgical stapler, an adhesive, and/or one or more other suitable mechanisms for affixing the catheter securement device to the patient's skin.

The methods of the present invention can be performed using any of the catheter securement device described herein. The method includes causing a bent profile in the catheter using the securement device to position the catheter at a desired angle and location. The methods described in Applicant's co-pending provisional applications 61/902,224 and 62/001,629, and PCT/US2012/036963 illustrate catheters and methods that can be applied to the securement devices described herein. The devices described herein may be used with any of the features described in 61/902,224; 62/001,629; and/or PCT/US2012/036963.

Some embodiments of the invention relate to securement device used for placement of a peripheral inserted central catheter (PICC). When used with a PICC, the securement device is used to turn the catheter up the arm, which results in less kinking and reduced pistoning of the catheter.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A catheter securement device for use in securing a central venous catheter in a vein, comprising:
  a device body defining a curved channel extending between a first end and a second end thereof, the curved channel having a diameter less than 3 mm and configured to accommodate a tubing of a central venous catheter having a size in a range from 2 French to 9 French,
    wherein the curved channel has a longitudinal opening with a size less than the diameter of the channel and the device body is made from a flexible material having a shore hardness less than 70 D, such that the longitudinal opening can be flexed open to accommodate a catheter having a diameter greater than that of the longitudinal opening; and
    wherein the device body has a surface that contacts the skin of a patient and is shaped to orient a free end of the tubing away from a direction of catheter insertion and to support a bent profile of the tubing with an angle in a range between 90° to 210° in a same plane as the surface that contacts the skin of the patient, thereby reducing the risk of kinking the tubing; and an adhesive or one or more eyelets, or both, coupled to the catheter clamp body for affixing the securement device to the skin of the patient.

2. The device of claim 1, further comprising a cover that slidably connects to the device body and covers the opening to the channel, thereby securing the catheter in the channel, wherein the cover and the base slide together in a direction transverse to the direction of the opening for inserting the catheter in the channel.

3. The catheter securement device of claim 2, wherein the body includes extensions that form undercuts and the cover includes flanges that slidably engage the extensions.

4. The catheter securement device of claim 1, wherein the curved channel has a radius of about 1.5 to about 5 cm.

5. The catheter securement device of claim 1, wherein the channel is configured to hold the catheter within the channel, the catheter having a size in a range from 5 French to 7 French and the diameter of the opening is less than 2 and ⅓ mm.

6. The catheter securement device of claim 1, wherein the curved channel is configured to engage a catheter with a size in a range from 7 French to 9 French.

7. The catheter securement device of claim 1, further comprising an antimicrobial material.

8. The catheter securement device of claim 1, wherein the device includes one or more eyelets coupled to the device body.

9. The device of claim 1, wherein the shore hardness of the body material is greater than 60 A and less than 50 D.

10. The device of claim 1, wherein the diameter of the channel is sized to grip a 7 French catheter.

11. A kit, comprising:
the central venous catheter as in claim 1;
one or more components for inserting the central venous catheter into a vein of a patient; and
the catheter securement device of claim 1.

12. The kit of claim 11, wherein the curved body defines a channel with a radius in a range from 1.5 to 5 cm.

13. The kit of claim 11, wherein the central venous catheter is a multi lumen catheter.

14. The kit of claim 11, wherein the one or more components for inserting the catheter includes one or more of a procedure tray, an anesthetic, a sterilizer for the patient's skin, a needle, a guide wire, a dilator, or a scalpel.

15. The kit of claim 11, further comprising a suture needle and a length of suture.

16. A method for securing a catheter to a patient's skin, the method comprising:
positioning the central venous catheter as in claim 1 in the superior vena cava of a patient;
positioning a free end of the central venous catheter in the catheter securement device of claim 1; and
securing the catheter securement device to the patient's skin.

17. The method of claim 16, wherein the catheter securement device is secured to the patient's skin with at least one suture or staple passing through at least one eyelet of the clamp and into the patient's skin.

18. The method of claim 16, wherein the catheter and the catheter securement device are secured at a jugular position.

19. The method of claim 16, wherein the size of the catheter is in a range from 5 French to 7 French and wherein the curve of the curved body of the securement device prevents kinking of the catheter in the channel.

20. The method of claim 16, wherein the catheter is a triple lumen catheter.

* * * * *